United States Patent [19]

Hodgson et al.

[11] Patent Number: 5,750,805
[45] Date of Patent: May 12, 1998

[54] REARRANGEMENT OF EPOXIDES

[75] Inventors: David Michael Hodgson, Reading; Jason Witherington, Harlow, both of United Kingdom

[73] Assignee: The University of Reading, Reading, Great Britain

[21] Appl. No.: 704,558

[22] PCT Filed: Mar. 15, 1995

[86] PCT No.: PCT/GB95/00553

§ 371 Date: Sep. 12, 1996

§ 102(e) Date: Sep. 12, 1996

[87] PCT Pub. No.: WO95/25079

PCT Pub. Date: Sep. 21, 1995

[30] Foreign Application Priority Data

Mar. 15, 1994 [GB] United Kingdom ............... 9405036

[51] Int. Cl.$^6$ .................................................. C07C 35/06
[52] U.S. Cl. .................................................. 568/838
[58] Field of Search ..................... 568/838; 564/364; 599/540

[56] References Cited

PUBLICATIONS

Milne et al., Dilithiated Aminoalcohols as Homochiral Bases, J. Chem. Soc. Chem Commun., pp. 884–886, May 21, 1993.

Hodgson et al., Highly Enantioselective Rearrangement of a meso–Epoxide to an Allyl Alcohol for Carbocyclic Nucleoside Synthesis: an Internal Alkoxide Effect, Tet. Assym., pp. 337–338, Mar. 1994.

Hodgson et al., Concise Racemic and Highly Enantioselective Approaches to Key Intermediates for the Synthesis of Carbocyclic Nucleosides and pseudo–Ribofuranoses:Formal Synthesis of Carbovir, Chem. Soc. Perkin Trans 1, pp. 3373–3378, Dec. 7, 1994.

Asami, Tetrahedron Letters, vol. 26, No. 47, pp. 5803–5806, 1985.

Primary Examiner—Gary Geist
Assistant Examiner—Karl J. Puttlitz, Jr.
Attorney, Agent, or Firm—Larson & Taylor

[57] ABSTRACT

Epoxides containing hydroxy groups are rearranged enantioselectively using a chiral base to give allyl alcohols in high enantiomeric excess, e.g.

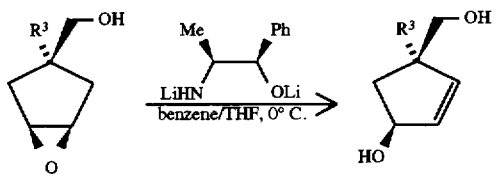

If $R^3 \neq H$, the reaction also has the effect of generating a chiral tetrasubstituted carbon atom.

14 Claims, No Drawings

REARRANGEMENT OF EPOXIDES

TECHNICAL FIELD

The present invention relates to the rearrangement of epoxides of cyclic olefins, generally leading to allyl alcohols. It particularly relates to the preparation of cyclic allyl alcohols by means of an enantioselective rearrangement of an epoxide employing a chiral base.

BACKGROUND ART

Some examples of this are already known. For example Milne, D. and Murphy, P. J., *J. Chem. Soc. Chem. Commun.*, (1993) 884–886 have recently disclosed the enantioselective rearrangement of a benzyloxy cyclopentene epoxide (1) using dilithiated (1R, 2S)-norephedrine: see Route A:

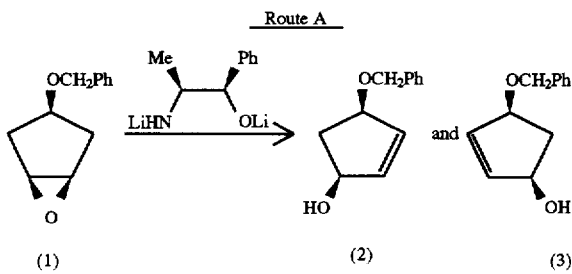

The enantiomeric allyl alcohols (2) and (3) were produced in unequal amounts, the greatest selectivity being achieved by allowing the reactants to warm from −78° C. to 0° C. over 16 h, which afforded the isomer (3) in 86% enantiomeric excess ('e.e.). That is, of the total amount of both isomers produced, 93% was isomer (3) and 7% was isomer (2) so that the e.e. of isomer (3) was 93−7=86%.

DISCLOSURE OF THE INVENTION

We were interested in producing individual enantiomers of cis-4-(hydroxymethyl)cyclopent-2-ene-1-ol (4),(5) and therefore attempted to perform an analogue of Route A, namely Route B ($R^1$=—$CH_2Ph$):

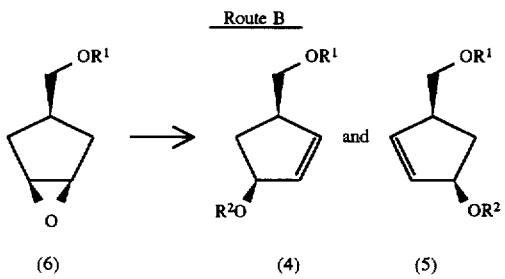

However, there was no reaction when the benzyloxyepoxide (6,$R^1$=—$CH_2Ph$) was treated with dilithiated (1R, 2S)-norephedrine. There was likewise no reaction with the corresponding trityloxy-epoxide (6, $R^1$=—$CPh_3$).

But we have surprisingly found that the unprotected hydroxy-epoxide (6,$R^1$=H) reacts smoothly to give the desired allyl alcohols (4 and 5; $R^1$=$R^2$=H). Furthermore either isomer (4 or 5) is obtainable almost exclusively (up to 95% e.e. or more). The asymmetric induction is in the opposite sense from that found in the prior art (Route A).

Thus according to the invention there is provided a process for the base-catalysed rearrangement of an epoxide to an unsaturated alcohol, wherein the epoxide is an epoxide of a cyclic olefin which has a free hydroxy group and wherein the rearrangement produces a pair of enantiomers and the base is chiral, the relative proportions of the pair of products being dependent on the chiral form of the base. We are particularly interested in the rearrangement of meso-compounds, generating asymmetry. Thus the substrate will usually have an odd number of atoms in the cyclic olefin ring, most usually 5 or 7. The hydroxy-group may then be a substituent on the cycloolefin ring. Alternatively it may be in a side-chain, e.g. —$CH_2OH$. Preferred substrates include cis-3-cyclopentene epoxide 1-methanol and cis-4-cycloheptene epoxide 1-methanol.

The base is preferably a metallated (e.g. lithiated) chiral base, particularly a chiral amine base. Examples of chiral amine bases include bis ((1R)-1-phenylethyl) amine. Without being limited to any mechanism, it seems likely that highly selective reaction is produced by means of a base that can interact simultaneously with the hydroxy group and the epoxide group. Thus a difunctional base e.g. a metallated 1,2-aminoalcohol such as a dilithiated enantiomer of ephedrine, norephedrine, pseudoephedrine or norpseudoephedrine may be most effective.

Reaction can be carried out under experimentally convenient conditions, e.g. mild temperatures (e.g. 0°–25° C.).

Furthermore we have found that the reaction can be applied to the generation of an asymmetric tetrasubstituted carbon atom by desymmetrisation of a meso-epoxide, e.g. Route C, where $R^3 \neq H$:

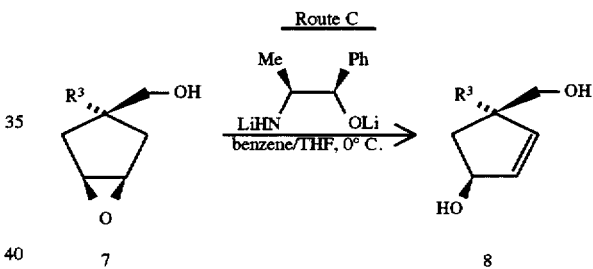

Thus in a preferred type of embodiment of the invention, the epoxide is an epoxide of a cycloolefin which is disubstituted at an atom located symmetrically with respect to the epoxide ring by (i) an interacting group such as a hydroxy group or a hydroxy-bearing group; and (ii) a second substituent which is not H. Thus a preferred substrate is (9), more preferably (10):

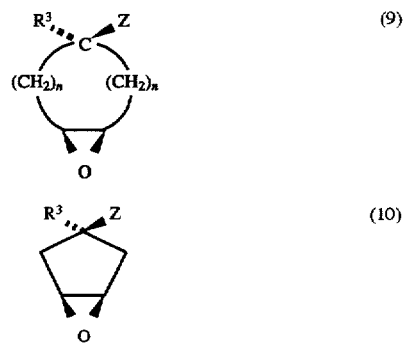

where Z is OH or a hydroxy-bearing side chain e.g. hydroxy alkyl (e.g. $C_{1-4}$ alkyl). $R^3$ may be alkyl, e.g. $C_{1-33}$ alkyl or substituted alkyl e.g. benzyl, or aryl or substituted aryl. n is an integer, generally 1 or 2. The methylene groups of the carbocyclic ring may be substituted, preferably symmetrically. Examples of suitable substrates include cis 1-methyl-3-cyclopentene epoxide 1-methanol, 1-butyl-3-cyclopentene epoxide 1-methanol, 1-[(4-methoxyphenyl)methoxymethyl]-3-cyclopentene epoxide 1-methanol, 1-butyl-3-cyclopentene epoxide 1-methanol, 1-[4-methoxyphenyl)methoxymethyl]-3-cyclopentene epoxide 1-methanol, 1-phenyl-3-cyclopentene epoxide 1-methanol, and 1-(4-methylphenyl)-3-cyclopentene epoxide 1-methanol.

The novel aryl-substituted epoxides may be prepared using well precedented chemical transformations from the corresponding aryl acetic acids. Thus 1-phenyl-3-cyclopentene epoxide 1-methanol was prepared by diallylation of phenylacetic acid (using lithium diisopropylamide and allyl bromide) followed by catalytic ring closing metathesis (Fu, Nguyen, S. T; and Grubbs, R. H., *J. Am. Chem. Soc.* 1993, 115, 9856–9857) reduction (LiAlH4) and hydroxyl-directed epoxidation.

MODES FOR CARRYING OUT THE INVENTION

EXAMPLE 1 cis-4-(hydroxymethyl)cyclopent-2-ene-1-ols(4 and 5, $R^1=R^2=H$

These compounds are useful synthetic reagents, e.g. for the preparation of carbocyclic nucleoside analogues which may be useful as therapeutic agents (c.f. the anti-HIV agent carbovir). We have prepared the individual enantiomers selectively by rearrangement of the cyclopentene epoxide (6, $R^1=H$), i.e. cis-6-oxabicyclo[3.1.0]hexane-3-methanol. This is a known compound which may be prepared by epoxidation of cyclopent-3-enemethanol (Corey, E. J. and De, B. *J. Am. Chem. Soc.* (1984), 106, 2735–2736), which may be made by reduction (LiAlH$_4$) of 3-cyclopentene carboxylic acid (Deprés, J.-P.; Greene, A. E., *J. Org. Chem.* (1984), 49, 928–931).

The epoxide (6, $R^1=H$) was treated with dilithiated (1R, 2S)-norephedrine (3 equivalents) in benzene: tetrahydrofuran (2:1, v/v) at 0° C., and warmed to room temperature over 24 hours. Conventional work-up then afforded the diol (4,$R^1=R^2=H$) in 65% yield, with an e.e. of 95%. (This was determined by bis-Mosher's ester analysis [(R)-MPTA, DCC, cat. DMAP, CH$_2$CHl$_2$, 92%: Dale J. A.; Dull, D. L.; Mosher, H. S. *J. Org. Chem.* (1969), 34, 2543–2549. Spectral comparisons were made with bis-Mosher's esters from a racemic mixture of the cis-diols 4 and 5 ($R^1=R^2=H$), prepared by treating the meso-epoxide 6($R^1=H$) with LDA.)

In a further example, the epoxide (6, $R^1=H$) was treated similarly but using dilithiated (1S, 2R)-norephedrine. This afforded the enantiomeric diol (5,$R^1=R^2=H$) in 57% yield, e.e.=95%.

The diols were acetylated in 95% yield (Ac$_2$O; pyridine, DMAP) to give the diacetates (4,5; $R^1=R^2=OAc$).

Experimental Details (a) cis-6-oxabicyclo[3.1.0]hexane-3-methanol(6,$R^1=H$):

t-butyl hydroperoxide [~3.0 mol dm$^{-3}$in CH$_2$Cl$_2$, prepared from a mixture of t-butyl hydroperoxide (70% by weight in water; 41 cm$^3$, 0.3 mol) and CH$_2$Cl$_2$(59 cm$^3$) by drying (2×MgSO$_4$) and storing over oven-dried 4A molecular sieves; 10 cm$^3$, ~30 mmol] was added dropwise to a stirred solution of 3-cyclopentene methanol (1.470 g, 15.0 mmol) and vanadyl acetylacetonate (15 mg, 0.06 mmol) in CH$_2$Cl$_2$ (40 cm$^3$) at 25° C. After 24 h aqueous sodium sulphite (15% w/v; 100 cm$^3$) was added and the reaction mixture was allowed to stir for a further 6 h. The reaction mixture was filtered, the filtrate was washed with aqueous sodium hydrogen carbonate (3×20 cm$^3$), brine (20 cm$^3$) and dried (MgSO$_4$). The solvent was evaporated under reduced pressure. Purification of the residue by bulb to bulb distillation gave a colourless oil, the meso-epoxide 6($R^1=H$) (1.677 g, 98%); b.p. 80°–100° C./2.0 mmHg; R$_f$0.30(ether); $v_{max}$cm$^{-1}$3400s, 2925s, 2855s and 1035s; $\delta_H$(400 MHz) 3.53 (2 H, s, 2×CHO), 3.46 (2 H, d, J 5, CH$_2$OH), 3.20(1 H, s, OH), 2.42–2.37 (1 H, m, CH) and 2.10–1.98 (4 H, m, 2×CH$_2$); $\delta_C$(100 MHz) 67.0 (2×CHO), 59.2 (CH$_2$OH), 36.6 (CH) and 31.2 (2×CH$_2$).

(b) cis-(1R)-4-Hydroxycyclopent-2-enemethanol (4;$R^1=R^2=H$):

n-Butyllithium (2.5 mol dm$^{-3}$ in hexanes; 6.5 cm$^3$, 16.2 mmol) was added dropwise to a stirred solution of (1R,2S)-norephedrine (1.221 g, 8.1 mmol) in benzene (15 cm$^3$) and THF (10 cm$^3$) at 0° C. After 0.5 h the meso-epoxide 6 ($R^1=H$)(0.276 g, 2.4 mmol), in THF (3 cm$^3$) was added dropwise to the reaction mixture over a period of 0.25 h. The solution was then allowed to warm to room temperature overnight. MeOH (10 cm$^3$) was added, the solution was filtered through Celite 545 (Fluka) and evaporated under reduced pressure. The residue was adsorbed onto SiO$_2$(1.0 g) and purified by suction-flash chromatography (gradient elution, ether to 10% ether-EtOAc, 40 cm$^3$ fractions) to give a colourless oil, the cis-(1R) diol 4($R^1=R^2=H$) (0.179 g, 65%); R$_f$ 0.25 (10% ether-EtOAc); $[\alpha]^{20}_D$ +46.7 (c 1.55 in CH$_2$Cl$_2$); $v_{max}$cm$^{-1}$3330s, 2930s, 1640w, 1140m, 1370m and 1040m; $\delta_H$(300 MHz) 5.98 (1 H, ddd, J 5.5, 2 and 2,=CH), 5.83 (1H, dd, J 5.5 and 2.5, CH=)4.67 (1 H, ddd, J 7, 2 and 2, CHO), 3.89–3.44 (2 H, m, OCH$_2$), 3.20–2.45 (3 H, m, 2×OH and CH), 2–2.27(1 H, m, H of CH$_2$) and 1.57 (1 H, ddd, J 14, 2 and 2, H of CH$_2$); $\delta_C$(69.5 MHz) 134.9 (=C), 134.8 (C=), 75.5 (CHO), 63.1 (OCH$_2$), 46.5 (CH) and 37.1 (CH$_2$).

(c) cis(1S)-4-Hydroxycyclopent-2-enemethanol:

Following the procedure for the cis-diol(4,$R^1=R^2=H$) using n-butyllithium (2.5 mol dm$^3$ in hexanes; 4.7 cm$^3$, 11.7 mmol), (1S,2R)-norephedrine (888 mg, 5.87 mmol) and the meso-epoxide 6($R^1=H$) (200 mg, 1.75 mmol), gave a colourless oil, the cis-1S diol 5($R^1=R^2=H$) (115 mg, 57%); $[\alpha]^{25}$ −44.3 (c 1.55 in CH$_2$Cl$_2$).

(d) cis-(1S)-1-[α-Methoxy-α-(trifluoromethyl)phenyl] acetoxy-4-{[α-methoxy-α-(trifluoromethyl)phenyl]-acetoxymethyl}cyclopent-2-ene.

A solution of the cis-(1R)-diol 4($R^1=R^2=H$)(28 mg, 0.25 mmol), 4-N,N-dimethylaminopyridine (8 mg, 0.06 mmol), (R)-α-methoxy-α-(trifluoromethyl)phenylacetic acid (120 mg, 0.51 mmol) and N,N'-dicyclohexylcarbodiimide (105 mg, 0.51 mmol) in CH$_2$Cl$_2$(5 cm$^3$) was stirred at 25° C. After 24 h the reaction mixture was filtered, the filter cake was washed with ether (3×10 cm$^3$) and the combined filtrates were washed with 1N hydrochloric acid (2×20 cm$^3$), saturated aqueous sodium hydrogen carbonate (2×20 cm$^3$), dried (MgSO$_4$), and evaporated under reduced pressure. Purification of the residue by column chromatography (20% ether-light petroleum) gave a colourless oil, the bis-Mosher's esters [126 mg, 94%, 1S:1R≧97.5:2.5 by $^1$H NMR analysis (in 4:1:1 CDCl$_3$: benzene-d$_6$:DMSO-d$_6$) of the diastereomeric H of CH$_2$'s in the δ 1.6–1.7 region]; R$_f$0.20 (20% ether-light petroleum); found: (M+NH$_4$), 564.1820, C$_{26}$H$_{28}$F$_6$NO$_6$ requires 564.17747; $v_{max}$cm$^{-1}$12960m, 1750s, 1450m, 1275s, 1175s and 1030s; m/z (CI) 564 (80%), 391 (35), 330 (86), 313 (72), 252 (45), 189 (68), 96 (54) and 79 (100); discernible data for major diastereomer: $\delta_H$(300 MHz) 7.61–7.25 (10 H,m, Ar), 6.10–5.91 (2 H, m, 2×CH=), 5.91–5.78 (1 H, m, CHO), 4.31–4.08 (2 H, m, OCH$_2$), 3.52 (3 H, s, J$_{H-F}$ not discernible Me), 3.51 (3 H, s, J$_{H-F}$ not discernible, Me), 3.08–3.04 (1 H, m, CH), 2.53 (1 H, ddd, J 14.5, 8.5 and 8.5, H of CH$_2$) and 1.70 (1 H, ddd, J 14.5, 3.5 and 3.5, H of CH$_2$); $\delta_C$(69.5 MHz) 167.7, (C=O), 167.6 (C=O), 137.7 (=C), 132.2 (Ar, quat.), 132.1 (Ar, quat.), 131.3 (C=), 129.5 (Ar), 129.4 (Ar), 128.9 (2×Ar), 128.8 (2×Ar), 127.3 (4×Ar), 125.2 (q, J$_{C-F}$288, 2×CF$_3$), 85.1 (q, J$_{CC-F}$28, 2×CCF$_3$), 81.4 (CHO), 68.7 (OCH$_2$), 55.4 (Me), 55.3 (Me), 43.5 (CH) and 33.0 (CH$_2$). Discernible data for minor diastereomer: $\delta_H$(300 MHz) 1.60 (1 H, ddd, J 14.5, 3.5 and 3.5, H of CH$_2$); $\delta_C$(69.5 MHz) 138.0 (=C), 131.2(C=), 81.3 (CHO), 68.8 (OCH$_2$), 43.4 (CH) and 32.9 (CH$_2$)

EXAMPLE 2

(1S,4R)-4-butyl-1-hydroxycyclopent-2-ene-4-methanol(8, R$^3$=Bu)

This is an example of Route C. The starting material (7,R$^3$=Bu) was prepared from 3-cyclopentene carboxylic acid (Depres and Greene, J. Org. Chem., 1984, 49, 928) via alkylation (BuI) of its dianion, followed by reduction (LiAlH$_4$) and epoxidation (t-butyl hydroperoxide and vanadyl acetylacetonate, as for Example 1). Other analogues (e.g. 7,R$^3$=Me) could be prepared analogously using different alkylating agents (e.g. MeI).

Rearrangement under similar conditions to those used in Example 1 gave the desired diol (8, R$^3$=Bu) in good yield (67%). Oxidation to enones and subsequent Mosher ester analysis showed that the e.e. of the product was similar to that attained in Example 1. Even the bulky butyl substituent does not affect efficiency. This strongly suggests that the enantiodiscriminating step occurs on the epoxide face of the cycloalkane.

Experimental Details

(1S,4R)-4-Butyl-1-hydroxycyclopent-2-ene-4-methanol 8 (R$^3$=Bu)

Following the procedure for the cis-diol 4 (R$^1$=R$^2$=H) using n-butyllithium (2.5 mol dm$^{-3}$ in hexanes; 3.5 cm$^3$, 8.8 mmol), (1R,2S)-norephedrine (0.67 g, 4.4 mmol) and the meso-epoxide 7(R$^3$=Bu)(0.276 g, 2.4 mmol), gave a colourless oil, the cis-diol 8 (R$^3$=Bu) (0.203 g, 67%); R$_f$0.38 (30% EtOAc-ether); found: (M+NH$_4$)$^+$, 188.1651, C$_{10}$H$_{22}$NO$_2$ requires 188.1651; [α]$^{20}_D$–28.9 (c 1.0 in CH$_2$Cl$_2$); $v_{max}$cm$^{-1}$3310s, 2927s, 1620w, 1380m and 1037m; $\delta_H$(400 MHz) 5.96 (1 H, dd, J 5 and 2,=CH), 5.62 (1 H, d, J 5, CH=), 4.68 (1 H, dd, J5 and 2, CHO), 3.45 (2 H, m, OCH$_2$), 3.30–2.92 (1 H, bs, OH), 2.89–2.15 (1 H, bs, OH), 1.95 (1 H, dd, J 6 and 2, H of CH$_2$), 1.62 (1 H, d, J 6, H of CH$_2$), 1.40–1.10 (6H, m, 3×CH$_2$); $\delta_C$(100 MHz) 139.6 (=CH) 133.9 (CH=), 75.7 (CHOH) 66.7 (CH$_2$OH), 53.9 (CCH$_2$OH), 42.1 (CH$_2$), 36.1 (CH$_2$), 26.5 (CH$_2$), 23.3 (CH$_2$) and 13.9 (CH$_3$); m/z (CI)139 (47%), 80 (100), 79(98) and 83(49).

EXAMPLE 3

(1S,4R)-4-Methyl-1-hydroxycyclopent-2-ene-4-methanol(8,R$^3$=Me)

Following the procedure of Example 1(b), the 4-methyl meso-epoxide (7,R$^3$=Me) (0.10 g, 0.78 mmol) was treated with a solution prepared from n-butyllithium(2.5 mol dm$^{-3}$ in hexanes; 1.56 cm$^3$, 3.90 mmol) and (1R,2S)-norephedrine (0.30 g, 1.95 mmol). This gave a colourless oil, the cis-diol 8 (R$^3$=Me) (0.063 g, 63%); R$_f$0.32 (30% EtOAc-ether); found: (M+H)$^+$, 129.0916, C$_7$H$_{13}$O$_2$ requires 129.0916; [α]$^{20}_D$–24.7 (c 1.0 in CH$_2$Cl$_2$); $v_{max}$cm$^{-1}$3310s, 2952s, 1669w, 1358m and 1042m; $\delta_H$(400 MHz) 5.97 (1 H, dd, J5 and 2, =CH), 5.66(1 H, d, J5, CH=), 4.72 (1 H, dd, J5 and 2, CHO), 3.47 (2 H, d, J5, OCH$_2$), 2.93–2.45 (1 H, bs, OH), 2.40–2.09 (1 H, bs, OH), 1.92 (1 H, dd, J7 and 2, H of CH$_2$), 1.75 (1 H, d, J7, H of CH$_2$), 1.04 (3H, s, CH$_3$); $\delta_C$(100 MHz) 140.7 (=CH) 133.9 (CH=), 75.9 (CHOH) 67.7 (CH$_2$OH), 50.1 (CCH$_2$OH), 45.0 (CH$_2$) and 23.1 (CH$_3$); m/z (EI) 111 (33%), 97 (26), 80 (100) and 79 (43).

We claim:

1. A process for the base-catalysed rearrangement of an epoxide to an unsaturated alcohol, wherein the epoxide is an epoxide of a cyclic olefin which has a free hydroxy group and wherein the rearrangement produces a pair of enantiomers and the base is chiral, the relative proportions of the pair of products being dependent on the chiral form of the base.

2. A process according to claim 1 wherein the cyclic olefin has a 5- or 7-membered carbocyclic ring.

3. A process according to claim 1 wherein the base is a metallated amine.

4. A process according to claim 1 wherein the base is a metallated aminoalcohol.

5. A process according to claim 4 wherein the aminoalcohol is a 1,2 aminoalcohol.

6. A process according to claim 5 wherein the aminoalcohol is norephedrine.

7. A process according to claim 6 wherein the base is dilithiated norephedrine.

8. A process according to claim 1 wherein epoxide is a meso-compound.

9. A process according to claim 1 wherein the hydroxy-group is a substituent on the cycloolefin ring or in a side-chain.

10. A process according to claim 9 wherein the cycloolefin ring has a —CH$_2$OH substituent which provides said free hydroxy group.

11. A process according to claim 9 wherein the cycloolefin ring includes an atom which is disubstituted, bearing both the hydroxy-group or hydroxy-side chain and a second (non-H) substituent.

12. A process according to claim 11 wherein the cycloolefin epoxide is a meso-compound, the cycloolefin ring containing an odd number of carbons and said disubstituted atom being symmetrically located relative to the epoxide ring.

13. A process according to claim 1 wherein the epoxide is cis-6-oxabicyclo[3.1.0]hexane-3-methanol and the unsaturated alcohol is cis-4-(hydroxymethyl)cyclopent-2-ene-1-ol.

14. A process according to claim 12 wherein the epoxide is of formula (10):

(10)

where R$^3$≠H and Z is OH or hydroxyalkyl.

* * * * *